United States Patent
Sands et al.

(10) Patent No.: US 10,610,270 B2
(45) Date of Patent: Apr. 7, 2020

(54) HYBRID INTRAMEDULLARY RODS

(71) Applicants: Steven Saam Sands, Edmond, OK (US); Christian Lutz, Heikendorf (DE); Axel Cremer, Fahrenkrug (DE); Stefan Völzow, Mönkeberg (DE); Klaus Dorawa, Kiel (DE)

(72) Inventors: Steven Saam Sands, Edmond, OK (US); Christian Lutz, Heikendorf (DE); Axel Cremer, Fahrenkrug (DE); Stefan Völzow, Mönkeberg (DE); Klaus Dorawa, Kiel (DE)

(73) Assignee: GLW, Inc., Waxhaw, NC (US)

( * ) Notice: Subject to any disclaimer, the term of this patent is extended or adjusted under 35 U.S.C. 154(b) by 0 days.

(21) Appl. No.: 16/248,150

(22) Filed: Jan. 15, 2019

(65) Prior Publication Data
US 2019/0216513 A1 Jul. 18, 2019

Related U.S. Application Data

(60) Provisional application No. 62/617,453, filed on Jan. 15, 2018.

(51) Int. Cl.
*A61B 17/72* (2006.01)
*A61B 17/88* (2006.01)

(52) U.S. Cl.
CPC .......... *A61B 17/7233* (2013.01); *A61B 17/72* (2013.01); *A61B 17/7208* (2013.01); *A61B 17/7216* (2013.01); *A61B 17/88* (2013.01)

(58) Field of Classification Search
CPC . A61B 17/7233; A61B 17/72; A61B 17/7208; A61B 17/7216; A61B 17/88

USPC .......................................................... 606/62
See application file for complete search history.

(56) References Cited

U.S. PATENT DOCUMENTS

| 2,136,471 | A | 11/1938 | Schneider |
| 2,987,062 | A | 6/1961 | Ellison |
| 3,272,204 | A | 9/1966 | Artandi et al. |
| 3,463,158 | A | 8/1969 | Schmitt et al. |
| 3,596,656 | A | 8/1971 | Kaute |

(Continued)

FOREIGN PATENT DOCUMENTS

| CN | 100341466 | 10/2007 |
| CN | 101128157 | 2/2008 |

(Continued)

OTHER PUBLICATIONS

European Patent Office "International Search Report and Written Opinion" for PCT international application PCT/US2019/013626, dated Apr. 30, 2019, pp. 1-12.

(Continued)

*Primary Examiner* — Pedro Philogene
*Assistant Examiner* — David C Comstock
(74) *Attorney, Agent, or Firm* — Buchanan Van Tuinen LLC

(57) ABSTRACT

The disclosure relates to medical devices and methods of manufacturing medical devices. An intramedullary rod includes a head member, a shaft member partially disposed within a distal recess of the head member, and an outer body member disposed circumferentially around the shaft member and a portion of the head member. Medical device systems and methods of manufacturing medical devices are also described.

20 Claims, 11 Drawing Sheets

(56) References Cited

U.S. PATENT DOCUMENTS

| | | | |
|---|---|---|---|
| 3,636,956 A | 1/1972 | Schneider | |
| 3,739,773 A | 6/1973 | Schmitt et al. | |
| 3,892,649 A | 7/1975 | Phillips et al. | |
| 3,918,100 A | 11/1975 | Shaw et al. | |
| 4,146,936 A | 4/1979 | Aoyagi et al. | |
| 4,186,448 A | 2/1980 | Brekke | |
| 4,192,021 A | 3/1980 | Deibig et al. | |
| 4,279,249 A | 7/1981 | Vert et al. | |
| 4,280,233 A | 7/1981 | Raab | |
| 4,292,694 A | 10/1981 | Koeneman | |
| 4,338,926 A | 7/1982 | Kummer et al. | |
| 4,457,301 A | 7/1984 | Walker | |
| 4,550,449 A | 11/1985 | Tunc | |
| 4,612,923 A | 9/1986 | Kronenthal | |
| 4,655,203 A | 4/1987 | Tormala et al. | |
| 4,733,654 A | 3/1988 | Marino | |
| 4,756,307 A | 7/1988 | Crowninshield | |
| 4,790,302 A | 12/1988 | Colwill et al. | |
| 4,851,008 A | 7/1989 | Johnson | |
| 4,863,475 A | 9/1989 | Andersen et al. | |
| 4,875,474 A | 10/1989 | Border | |
| 4,898,186 A | 2/1990 | Ikada et al. | |
| 4,911,153 A | 3/1990 | Border | |
| 4,919,666 A | 4/1990 | Buchhorn et al. | |
| 4,943,292 A | 7/1990 | Foux | |
| 4,968,317 A | 11/1990 | Tormala et al. | |
| 4,973,333 A | 11/1990 | Treharne | |
| 5,057,110 A | 10/1991 | Kranz et al. | |
| 5,057,111 A | 10/1991 | Park | |
| 5,084,050 A | 1/1992 | Draenert | |
| 5,084,051 A | 1/1992 | Tormala et al. | |
| 5,108,399 A | 4/1992 | Eitenmuller et al. | |
| 5,122,141 A * | 6/1992 | Simpson | A61B 17/72 606/62 |
| 5,127,913 A | 7/1992 | Thomas, Jr. | |
| 5,181,930 A * | 1/1993 | Dumbleton | A61F 2/30965 623/23.34 |
| 5,236,431 A | 8/1993 | Gogolewski et al. | |
| 5,275,601 A | 1/1994 | Gogolewski et al. | |
| 5,292,695 A | 3/1994 | Galloway | |
| 5,484,438 A | 1/1996 | Pennig | |
| 5,514,137 A | 5/1996 | Coutts | |
| 5,741,266 A | 4/1998 | Moran et al. | |
| 5,776,194 A | 7/1998 | Mikol et al. | |
| 5,792,400 A | 8/1998 | Talja et al. | |
| 5,810,821 A | 9/1998 | Vandewalle | |
| 5,855,579 A * | 1/1999 | James | A61B 17/1717 606/304 |
| 5,868,746 A | 2/1999 | Sarver et al. | |
| 5,871,484 A | 2/1999 | Spievack et al. | |
| 5,895,390 A | 4/1999 | Moran et al. | |
| 5,928,267 A | 7/1999 | Bonutti et al. | |
| 5,935,127 A | 8/1999 | Border | |
| 6,004,323 A | 12/1999 | Park et al. | |
| 6,296,645 B1 | 10/2001 | Hover et al. | |
| 6,402,753 B1 | 6/2002 | Cole et al. | |
| 6,702,816 B2 | 3/2004 | Buhler | |
| 6,709,436 B1 | 3/2004 | Hover et al. | |
| 6,783,529 B2 | 8/2004 | Hover et al. | |
| 6,786,908 B2 | 9/2004 | Hover et al. | |
| 6,808,527 B2 | 10/2004 | Lower et al. | |
| 7,001,386 B2 | 2/2006 | Sohngen et al. | |
| 7,232,442 B2 | 6/2007 | Sohngen et al. | |
| 7,410,488 B2 | 8/2008 | Janna et al. | |
| 7,481,839 B2 | 1/2009 | Zucherman et al. | |
| 7,588,577 B2 | 9/2009 | Fencl et al. | |
| 7,591,819 B2 | 9/2009 | Zander et al. | |
| 7,655,009 B2 | 2/2010 | Grusin | |
| 7,699,879 B2 | 4/2010 | Sherman et al. | |
| 7,713,271 B2 | 5/2010 | Warburton | |
| 7,753,913 B2 | 7/2010 | Szakelyhidi, Jr. et al. | |
| 7,846,162 B2 | 12/2010 | Nelson et al. | |
| 7,850,690 B2 | 12/2010 | Frigg et al. | |
| 7,850,717 B2 | 12/2010 | Dewey et al. | |
| 7,892,234 B2 | 2/2011 | Schlienger et al. | |
| 7,909,825 B2 | 3/2011 | Saravia et al. | |
| 7,914,533 B2 | 3/2011 | Nelson et al. | |
| D638,125 S | 5/2011 | Velikov | |
| D638,126 S | 5/2011 | Velikov | |
| 7,942,875 B2 | 5/2011 | Nelson et al. | |
| 7,947,043 B2 | 5/2011 | Mutchler | |
| 8,034,056 B2 | 10/2011 | Fencl et al. | |
| 8,048,134 B2 | 11/2011 | Partin | |
| 8,066,706 B2 | 11/2011 | Schlienger et al. | |
| 8,083,742 B2 | 12/2011 | Martin | |
| 8,092,453 B2 | 1/2012 | Warburton | |
| 8,092,505 B2 | 1/2012 | Sommers | |
| 8,100,910 B2 | 1/2012 | Warburton | |
| 8,109,930 B2 | 2/2012 | Schlienger et al. | |
| 8,157,802 B2 | 4/2012 | Elghazaly et al. | |
| 8,221,419 B2 | 7/2012 | Frigg et al. | |
| 8,287,539 B2 | 10/2012 | Nelson et al. | |
| 8,287,541 B2 | 10/2012 | Nelson et al. | |
| 8,303,590 B2 | 11/2012 | Elghazaly et al. | |
| 8,377,062 B2 | 2/2013 | Lutz et al. | |
| 8,394,103 B2 | 3/2013 | O'Reilly et al. | |
| 8,435,238 B2 | 5/2013 | Dejardin | |
| 8,435,239 B2 | 5/2013 | Lutz et al. | |
| 8,454,606 B2 | 6/2013 | Frigg et al. | |
| 8,460,294 B2 | 6/2013 | Overes | |
| 8,465,489 B2 | 6/2013 | Schlienger et al. | |
| RE44,501 E | 9/2013 | Janna et al. | |
| 8,556,896 B2 | 10/2013 | Kitch et al. | |
| 8,663,224 B2 | 3/2014 | Overes et al. | |
| 8,668,695 B2 | 3/2014 | Schwammberger et al. | |
| 8,709,055 B2 | 4/2014 | Beyar et al. | |
| 8,771,283 B2 | 7/2014 | Larsen et al. | |
| 8,784,430 B2 | 7/2014 | Kay et al. | |
| 8,888,779 B2 | 11/2014 | Senn et al. | |
| 8,961,516 B2 | 2/2015 | Nelson et al. | |
| 9,039,707 B2 | 3/2015 | Kaup | |
| 8,998,987 B2 | 4/2015 | Wallick | |
| 9,101,417 B2 | 8/2015 | Beyar et al. | |
| 9,174,390 B2 | 11/2015 | Lechmann et al. | |
| 9,237,909 B2 | 1/2016 | Schlienger et al. | |
| 9,320,551 B2 | 4/2016 | Frank et al. | |
| RE46,008 E | 5/2016 | Janna et al. | |
| RE46,078 E | 7/2016 | Janna et al. | |
| 9,433,448 B2 | 9/2016 | Ehmke et al. | |
| 9,433,451 B2 | 9/2016 | Ehmke et al. | |
| 9,439,695 B2 | 9/2016 | Wolter | |
| 9,440,379 B2 | 9/2016 | Smith et al. | |
| 9,451,971 B2 | 9/2016 | Warburton et al. | |
| 9,452,001 B2 | 9/2016 | Faccioli et al. | |
| 9,463,055 B2 | 10/2016 | Ehmke et al. | |
| 9,474,557 B2 | 10/2016 | Schwammberger et al. | |
| 9,526,542 B2 | 12/2016 | Ehmke | |
| 9,549,767 B2 | 1/2017 | Lutz et al. | |
| 9,572,606 B2 | 2/2017 | Frank et al. | |
| 9,597,128 B2 | 3/2017 | Boileau et al. | |
| 9,597,129 B2 | 3/2017 | Keller et al. | |
| 9,642,658 B2 | 5/2017 | Boyd et al. | |
| 9,662,153 B2 | 5/2017 | Larsen et al. | |
| 9,662,154 B2 | 5/2017 | Kaup | |
| 9,681,901 B2 | 6/2017 | Wolter | |
| 9,737,347 B2 | 8/2017 | Schlienger et al. | |
| 9,770,273 B2 | 9/2017 | Guitelman | |
| 9,770,278 B2 | 9/2017 | Lappin | |
| 9,782,206 B2 | 10/2017 | Mueckter et al. | |
| 9,814,499 B2 | 11/2017 | Buscaglia et al. | |
| 9,814,500 B2 | 11/2017 | Frigg et al. | |
| 10,022,164 B2 | 7/2018 | Mangiardi | |
| 10,022,165 B2 | 7/2018 | Mangiardi | |
| 10,028,777 B2 | 7/2018 | Beyar et al. | |
| 2003/0099683 A1 | 5/2003 | Grunze | |
| 2005/0085812 A1 | 4/2005 | Sherman et al. | |
| 2006/0064095 A1 | 3/2006 | Senn et al. | |
| 2006/0084997 A1 | 4/2006 | Dejardin | |
| 2006/0095039 A1 | 5/2006 | Mutchler | |
| 2006/0149248 A1 | 7/2006 | Schlienger et al. | |
| 2006/0161155 A1 | 7/2006 | Schlienger et al. | |
| 2006/0189988 A1 | 8/2006 | Schlienger et al. | |
| 2006/0200142 A1 | 9/2006 | Sohngen et al. | |
| 2006/0235394 A1 | 10/2006 | Martin | |

(56) References Cited

U.S. PATENT DOCUMENTS

| | | |
|---|---|---|
| 2006/0235395 A1 | 10/2006 | Frigg et al. |
| 2006/0241605 A1 | 10/2006 | Schlienger et al. |
| 2006/0247638 A1 | 11/2006 | Trieu et al. |
| 2007/0049938 A1 | 3/2007 | Wallace et al. |
| 2007/0049939 A1 | 3/2007 | Wallace et al. |
| 2007/0049940 A1 | 3/2007 | Wallace et al. |
| 2007/0156144 A1 | 7/2007 | Ulrich et al. |
| 2007/0270855 A1 | 11/2007 | Partin |
| 2007/0276385 A1 | 11/2007 | Schlienger et al. |
| 2007/0288019 A1 | 12/2007 | Schlienger et al. |
| 2008/0221577 A1 | 9/2008 | Elghazaly |
| 2008/0255558 A1 | 10/2008 | Schlienger et al. |
| 2008/0262496 A1 | 10/2008 | Schlienger et al. |
| 2008/0294164 A1 | 11/2008 | Frank et al. |
| 2009/0043307 A1 | 2/2009 | Faccioli et al. |
| 2010/0152740 A1 | 6/2010 | O'Reilly et al. |
| 2010/0174284 A1 | 7/2010 | Schwammberger et al. |
| 2010/0179551 A1 | 7/2010 | Keller et al. |
| 2010/0249782 A1 | 9/2010 | Durham |
| 2011/0046625 A1 | 2/2011 | Boileau et al. |
| 2011/0150962 A1 | 6/2011 | Lutz et al. |
| 2011/0152863 A1 | 6/2011 | Lutz et al. |
| 2011/0178465 A1 | 7/2011 | Boyd et al. |
| 2011/0184417 A1 | 7/2011 | Kitch et al. |
| 2011/0208189 A1 | 8/2011 | Faccioli et al. |
| 2011/0245832 A1 | 10/2011 | Giersch et al. |
| 2013/0053849 A1 | 2/2013 | Kaup |
| 2013/0231610 A1 | 9/2013 | Lutz et al. |
| 2014/0105776 A1 | 4/2014 | Ellero et al. |
| 2014/0135769 A1* | 5/2014 | Ziran ............... A61B 17/72 606/63 |
| 2014/0188113 A1 | 7/2014 | Overes et al. |
| 2014/0194877 A1 | 7/2014 | Mangiardi |
| 2014/0296853 A1 | 10/2014 | Wolter |
| 2014/0296854 A1 | 10/2014 | Wolter |
| 2014/0309637 A1 | 10/2014 | Dejardin |
| 2015/0045792 A1 | 2/2015 | Manigardi |
| 2015/0142125 A1 | 5/2015 | Watanabe et al. |
| 2015/0272636 A1* | 10/2015 | Schwammberger ................. A61B 17/7241 606/62 |
| 2016/0310176 A1 | 10/2016 | Van Dyke et al. |
| 2017/0042592 A1 | 2/2017 | Kim |
| 2017/0079699 A1 | 3/2017 | Fallin et al. |
| 2017/0105776 A1 | 4/2017 | Lutz |
| 2019/0053836 A1 | 2/2019 | Sweeney et al. |
| 2019/0216513 A1 | 7/2019 | Sands et al. |
| 2019/0282279 A1* | 9/2019 | Rains ............... A61B 17/80 |

FOREIGN PATENT DOCUMENTS

| | | |
|---|---|---|
| CN | 100457058 | 2/2009 |
| CN | 101426444 | 5/2009 |
| CN | 102008751 | 1/2014 |
| CN | 101686844 | 5/2014 |
| CN | 102355863 | 9/2014 |
| EP | 1265653 | 6/2004 |
| FR | 2710835 | 10/1993 |
| JP | 1995213534 | 8/1995 |
| JP | 2009515612 | 4/2009 |
| JP | 4357478 | 11/2009 |
| JP | 4436320 | 3/2010 |
| JP | 4417328 | 12/2010 |
| JP | 4684662 | 5/2011 |
| JP | 5357546 | 12/2013 |
| SU | 1692566 | 5/1989 |
| WO | WO1998018397 | 5/1998 |
| WO | WO2004024012 | 3/2004 |
| WO | WO2004110290 | 12/2004 |
| WO | WO2005102196 | 11/2005 |
| WO | WO2007101267 | 9/2007 |
| WO | WO2008134264 | 11/2008 |
| WO | WO2011082152 | 7/2011 |
| WO | WO2012065068 | 5/2012 |
| WO | WO2014015262 | 1/2014 |
| WO | WO2015144131 | 1/2015 |
| WO | WO2015137911 | 9/2015 |

OTHER PUBLICATIONS

Patent Office of the China State Intellectual Property Office, "Notice on the First Office Action" for Chinese application No. 201580015397.4, dated Feb. 5, 2018, pp. 1-8.

Patent Office of the China State Intellectual Property Office, "Notice on the First Office Action" for Chinese application No. 201580015397A, dated Feb. 5, 2018, pp. 1-4, English translation.

* cited by examiner

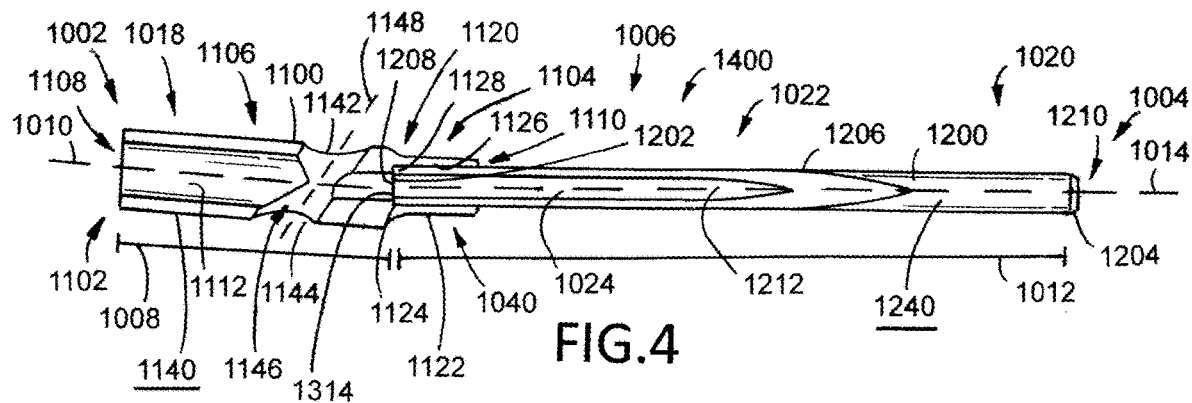
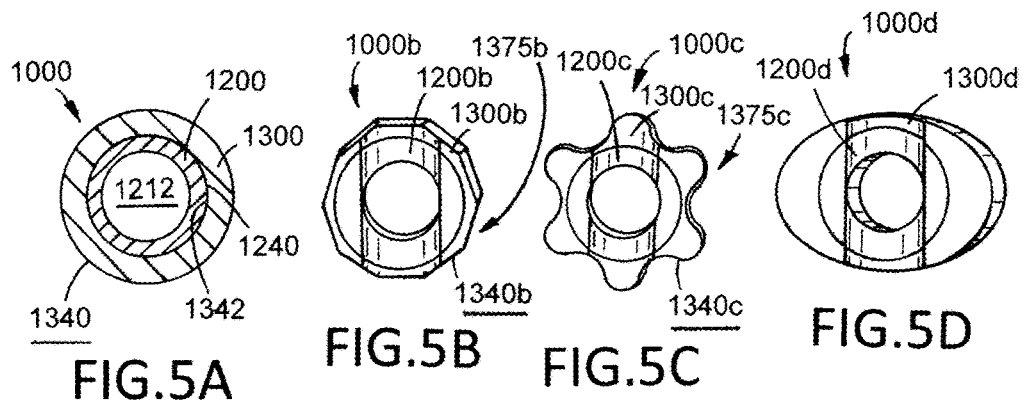
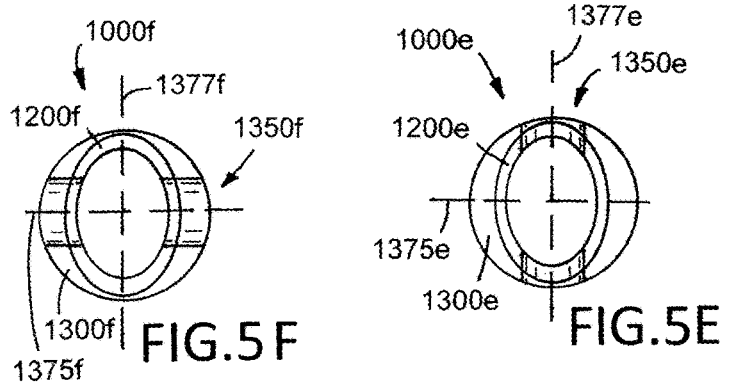
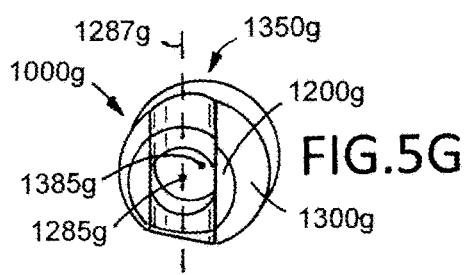

HYBRID INTRAMEDULLARY RODS

CROSS-REFERENCE TO RELATED APPLICATIONS

This application claims benefit to the U.S. Provisional Patent Application No. 62/617,453, filed Jan. 15, 2018, which is incorporated by reference into this disclosure in its entirety.

FIELD

The disclosure relates to the field of medical devices. More particularly, the disclosure relates to implantable medical devices useful for orthopedic applications. Specific examples relate to intramedullary rods, which are commonly referred to as intramedullary nails. The disclosure also relates to medical device systems and methods of manufacturing medical devices.

BACKGROUND

Intramedullary rods, also referred to as intramedullary nails or bone nails, are implantable medical devices that are commonly used for fracture stabilization and fixation. These devices can be made from a variety of materials and can include structural adaptations that facilitate their use and/or enhance their performance.

While intramedullary rods are known, the inclusion of multiple materials in the construction of an intramedullary rod typically results in handling and performance drawbacks.

A need remains, therefore, for improved hybrid intramedullary rods.

BRIEF SUMMARY OF SELECTED EXAMPLES

Various example medical devices are described.

An example intramedullary rod comprises a head member, a shaft member partially disposed within the distal recess of the head member, and an outer body member disposed circumferentially around the shaft member and a portion of the head member.

Another example intramedullary rod comprises a head member having a proximal head member end, a distal head member end, a head member distal extension defining a head member cavity, a head member lumen extending between the proximal head member end and the distal head member end, and a head member outer surface, a first opening on a first axial side of the head member, a second opening on a second axial side of the head member, and a passageway extending between the first opening and the second opening; a shaft member having a shaft member proximal end disposed within the head member cavity, the shaft member having a proximal shaft member opening, a distal shaft member opening, and defining a shaft member lumen extending between the proximal shaft member opening and the distal shaft member opening, the shaft member lumen positioned in line with the head member lumen; and an outer body member disposed circumferentially around the shaft member and a portion of the head member.

Another example intramedullary rod comprises a head member defining a recess, a first opening having a first inner diameter, a second opening, and a passageway extending between the first and second openings; a shaft member partially disposed within the recess of the head member; and an outer body member disposed circumferentially around the shaft member and a portion of the head member, the outer body member defining a third opening disposed adjacent the first opening of the head member and providing access to the passageway, the third opening having a second inner diameter that is less than the first inner diameter.

Another example intramedullary rod comprises a head member defining a recess, a first opening having a first inner diameter, a second opening, and a passageway extending between the first and second openings; a shaft member partially disposed within the recess of the head member; and an outer body member disposed circumferentially around the shaft member and a portion of the head member, the outer body member defining a third opening disposed adjacent the first opening of the head member and providing access to the passageway, the third opening having a second inner diameter that is the same as the first inner diameter.

Various example medical device systems are described.

An example medical device system comprises a plurality of a head members and a plurality of shaft members. The head members are identical to each other. Each of the shaft members has a different axial length than the axial length of the other shaft members.

Various example methods of manufacturing medical devices are described.

An example method of manufacturing an intramedullary rod comprises forming a shaft member from a precursor; securing the shaft member to a selected head member; and overmolding the shaft member with a suitable material to form an intramedullary rod having an outer body member disposed circumferentially about the shaft member and a portion of the head member.

Another example method of manufacturing an intramedullary rod comprises forming a shaft member from a precursor; securing the shaft member to a head member defining a recess, a first opening having a first inner diameter, a second opening, and a passageway extending between the first and second openings; and overmolding the shaft member with a suitable material to form an intramedullary rod having an outer body member disposed circumferentially about the shaft member and around the first opening of the head member.

Another example method of manufacturing an intramedullary rod comprises selecting one head member from a medical device system comprising a two or more identical head members and two or more shaft members having different axial lengths; selecting one shaft member from the two or more shaft members of the medical device system; securing the selected shaft member to the selected head member; overmolding the shaft member with a suitable material to form an intramedullary rod having an outer body member disposed circumferentially about the shaft member and a portion of the head member.

Additional understanding of the inventive medical devices, medical device systems, and methods of manufacturing medical devices can be obtained by reviewing the detailed description of selected examples, below, with reference to the appended drawings.

DESCRIPTION OF FIGURES

FIG. 4 is longitudinal cross-sectional view of a head-shaft assembly of the first example intramedullary rod.

FIG. 5A is a sectional view of the first example intramedullary rod taken along line 5A-5A in FIG. 1.

FIG. 5B is a sectional view of an alternative intramedullary rod.

FIG. 5C is a sectional view of another alternative intramedullary rod.

FIG. 5D is a sectional view of another alternative intramedullary rod.

FIG. 5E is a sectional view of another alternative intramedullary rod.

FIG. 5F is a sectional view of another alternative intramedullary rod.

FIG. 5G is a sectional view of another alternative intramedullary rod.

DETAILED DESCRIPTION OF SELECTED EXAMPLES

Figure 1:
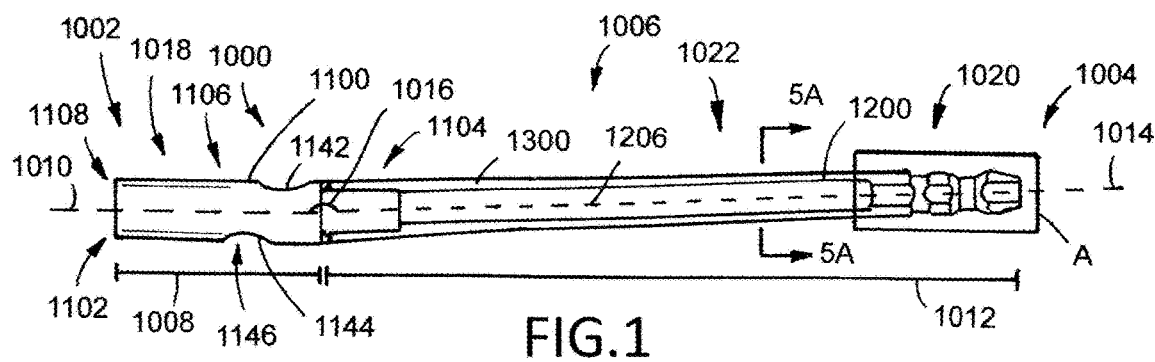
FIG. 1 is a side view of a first example intramedullary rod.

The following detailed description and the appended drawings describe and illustrate various example medical devices and methods. The description and illustration of these examples enable one skilled in the art to make and use examples of the inventive medical devices and to perform examples of the inventive methods. They do not limit the scope of the claims in any manner.

As used herein, the term "lumen," and grammatically related terms, refers to the inside space of a tubular structure. The term does not require any specific dimensions, relative dimensions, configuration, or regularity.

As used herein, the term "circumferential," and grammatically related terms, refers to a structural arrangement of one structure relative to another structure, feature, or property of another structure. The term does not require any specific dimensions, relative dimensions, configuration, or regularity of either structure.

FIGS. 1, 2, 3, 4, and 5A illustrate a first example intramedullary rod 1000 or a portion of the first example intramedullary rod 1000. The intramedullary rod 1000 has a proximal end 1002, a distal end 1004, and a body 1006 extending between the proximal end 1002 and the distal end 1004. A first portion 1008 of the intramedullary rod 1000 extends along a first longitudinal axis 1010, and a second portion 1012 of the intramedullary rod 1000 extends along a second longitudinal axis 1014. In the illustrated example, the first 1010 and second 1014 longitudinal axes intersect at a non-linear angle 1016. The intramedullary rod 1000 includes a head portion 1018 located at the proximal end 1002, a tip portion 1020 located at the distal end 1004, and a shaft portion 1022 extending between the head portion 1018 and the tip portion 1020 and comprising the body 1006. Also, the intramedullary rod 1000 includes a head member 1100, a shaft member 1200 partially disposed within the head member 1100, and an outer body member 1300 disposed circumferentially around the shaft member 1200 and a portion of the head member 1100. A device lumen 1024 extends through the entire axial length of the intramedullary rod 1000 from a proximal opening 1102 of the head member 1100 to a distal opening 1210 of the shaft member 1200, placing the entire device lumen 1024 in communication with the environment external to the intramedullary rod 1000. As such, the intramedullary rod 1000 is a cannulated rod, allowing it to be passed over a separate member, such as a wire, to facilitate placement and/or positioning during implantation.

The head portion 1018 provides structure for receiving a bone screw, such as a locking or lag screw commonly used in the stabilization and fixation of bone fractures, such as hip fractures. The tip portion 1020 provides structure for interfacing with the medullary canal of a bone, such as a femur, during placement, as well as structure for receiving distal locking screws commonly used in the stabilization and fixation of bone fractures, such as hip fractures.

The head member 1100 has a proximal end 1102, a distal end 1104, and a body 1106 extending between the proximal end 1102 and the distal end 1104. The proximal end 1102 defines a proximal opening 1108 and the distal end 1104 defines a distal opening 1110. As best illustrated in FIG. 4, the head member 1100 defines a head member lumen 1112 extending between the proximal opening 1108 and the distal opening 1110. In the assembled intramedullary rod 1000, the proximal opening 1108 provides access to the head member lumen 1112 from the environment external to the intramedullary rod 1000 and the distal opening 1110 receives a portion of the shaft member 1200 in a manner that positions the head member lumen 1112 in line with the shaft member lumen 1212 defined by the shaft member 1200 to form device lumen 1024. In use, the intramedullary rod 1000 can be passed over a previously-placed wire such that the wire extends through the head member lumen 1112 and, ultimately, through device lumen 1024 if desired or necessary. The intramedullary rod 1000 can then be advanced over the wire to a desired degree to achieve a desired placement and/or positioning before securing the intramedullary rod 1000 within the medullary cavity.

The distal end 1104 of the head member 1100 defines a circumferential shoulder 1120 that forms a distal extension 1122 having a smaller outer diameter than the outer diameter of the portion of the body 1106 that is on the proximal side of the circumferential shoulder 1120. The distal extension 1122 defines a cavity 1124 that is bounded by a circumferential wall 1126 and a transverse wall 1128. The circumferential wall 1126 surrounds the second longitudinal axis 1014 of the intramedullary rod 1000. As best illustrated in FIG. 4, the transverse wall 1128 defines inner opening 1130 that transitions the inner diameter of the head member lumen 1112 from the larger inner diameter 1132 of the portion of the body 1106 of the head member 1100 that is proximal to the circumferential shoulder 1120 to the smaller inner diameter 1134 of the portion of the body 1106 of the head member 1100 that is distal to the circumferential shoulder 1120.

The circumferential wall 1124 defines structure that facilitates formation of an interface 1040 between the head member 1100 and the shaft member 1200. The transverse wall 1126 may also define structure that facilitates such interaction. As such, the circumferential wall 1126, the transverse wall 1128, and, as a result, the cavity 1124 may have any suitable configuration and a skilled artisan will be able to select an appropriate configuration for each of these structures in an intramedullary rod according to a particular embodiment based on various considerations, including the configuration and nature of the shaft member included in the intramedullary rod. Examples of suitable configurations include circular, splined, and other configurations. In this example, as best illustrated in FIG. 4, the circumferential wall 1126 is circular and smooth, such that cavity 1124 has a cylindrical form.

Figure 2:
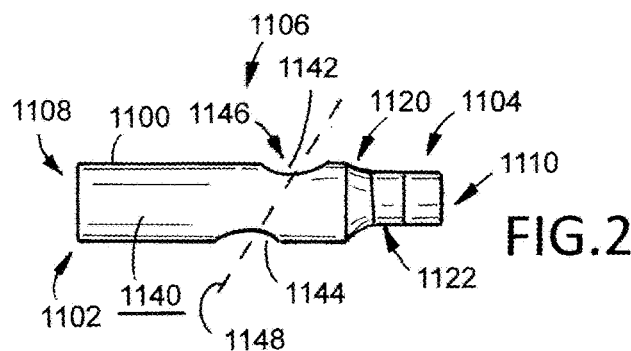
FIG. 2 is an isolated side view of the head member of the first example intramedullary rod.

The body 1106 of the head member 1100 has an outer surface 1140 that defines a first opening 1142 on a first axial side of the body 1106 and a second opening 1144 positioned a second, opposite axial side of the body 1106. A passageway 1146 extends from the first opening 1142 to the second opening 1144. As best illustrated in FIGS. 2 and 4, the passageway 1146 extends along an axis 1148 that is disposed at a transverse angle to the first longitudinal axis 1010 of the intramedullary rod 1000. The passageway is sized and configured to receive a lag screw used for securing the intramedullary rod 1000 to a bone.

The shaft member 1200 has a proximal end 1202, a distal end 1204, and a body 1206 extending between the proximal end 1202 and the distal end 1204. The proximal end 1202 defines a proximal opening 1208 and the distal end 1204 defines a distal opening 1210. As best illustrated in FIG. 4, the shaft member 1200 defines a shaft member lumen 1212 extending between the proximal opening 1208 and the distal opening 1210. Thus, the shaft member 1200 is a tubular member. The proximal end 1202 of the outer body member 1200 has a proximal engaging surface 1214 that is in contact interface with the transverse wall 1128 within the cavity 1124 of the head member 1100. In the assembled intramedullary rod 1000, the distal opening 1210 provides access to the shaft member lumen 1212 from the environment external to the intramedullary rod 1000 and the proximal end 1202 is disposed within the cavity 1124 of the head member 1100 in a manner that positions the shaft member lumen 1212 in line with the head member lumen 1112 defined by the head member 1100 to form device lumen 1024.

The shaft member 1200 has an outer surface 1240. As described in detail below, the outer body member 1300 circumferentially surrounds the shaft member 1200 and is in contact with the outer surface 1240. The outer surface 1240 can be treated in a manner that prepares the shaft member 1200 for bonding, contact, or other interface with the outer body member 1300. If a surface treatment is included, any suitable surface treatment can be used and a skilled artisan will be able to select a suitable surface treatment for an intramedullary rod according to a particular embodiment based on various considerations, such as the materials of the head member and shaft member of the intramedullary rod. Examples of suitable surface treatments include roughening, etching, and other surface treatments. Also, the portion of the outer surface on the proximal end of the shaft member can be left untreated or treated in a different manner than the remainder of the shaft member in an intramedullary rod according to a particular embodiment if desirable or necessary, such as to facilitate formation of a head-shaft assembly.

The outer body member 1300 has a proximal end 1302, a distal end 1304, and a body 1306 extending between the proximal end 1302 and the distal end 1304. The outer body member 1300 is a tubular member disposed circumferentially around the shaft member 1200 and the distal extension 1122 of the head member 1100. Thus, the proximal end 1302 defines a proximal opening 1308 and the distal end 1304 defines a distal opening 1310. The outer body member 1300 defines a lumen 1308 extending between the proximal opening 1308 and the distal opening 1310. The outer body member 1300 has an outer surface 1340 and an inner surface 1342. As best illustrated in FIG. 5A, the body 1206 of the shaft member 1200 is disposed within the lumen 1308 of the outer body member 1300 such that the inner surface 1342 of the outer body member 1300 is in contact interface with the outer surface 1240 of the shaft member 1200.

Figure 1A:
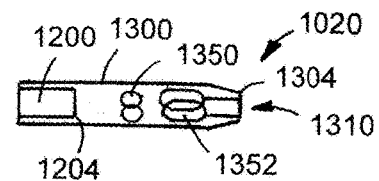
FIG. 1A is a magnified view of Area A of FIG. 1.

As best illustrated in FIG. 1A, the distal end 1304 of the outer body member 1300 defines first 1350 and second 1352 locking screw passageways that extend through the outer body member 1300 from one side to the other. The locking screw passageways 1350, 1352 are sized and configured for receiving distal locking screws commonly used in the stabilization and fixation of bone fractures, such as hip fractures. While optional, inclusion of locking screw passageways is considered advantageous to facilitate securement of the intramedullary rod 1000 to bone during placement. Also, any suitable number of locking screw passageways can be included in an intramedullary rod according to a particular embodiment and a skilled artisan will be able to select an appropriate number of locking screw passageways for a particular embodiment based on various considerations, including any number of locking screws considered desirable or potentially necessary for use of the intramedullary rod in stabilization and/or fixation of a particular bone fractures.

As illustrated in FIG. 4, a head-shaft assembly 1400 is formed when the proximal end 1202 of the shaft member 1200 is disposed within the cavity 1124 of the head member

1100. This can be accomplished by any suitable technique or process for placing the proximal end 1202 of the shaft member 1200 within the cavity 1124 of the head member 1100 and securing the shaft member 1200 to the head member 1100, such as press fitting the components together, shrinking the head member cavity 1124 around the proximal end 1202 of the shaft member 1200, welding, or other suitable technique or process.

It is noted that angle 1016 can comprise any suitable angle, and the illustrated non-linear angle is merely an example. A linear or substantially linear angle can be used, as can other suitable angles.

Each of the shaft member and outer body member in an intramedullary rod according to an embodiment can have any suitable configuration and a skilled artisan will be able to select an appropriate configuration for each of these elements for a particular embodiment based on various considerations, including the nature of the medullary canal of the bone or bone type with which the intramedullary rod is intended to be used. As best illustrated in FIG. 5A, each of the shaft member 1200 and the outer body member 1300 in intramedullary rod 1000 has a circular cross-sectional shape. Also, outer body member 1300 is disposed circumferentially and coaxially around the shaft member 1200.

Each of FIGS. 5B through 5G illustrates an alternative intramedullary rod having a shaft member and outer body member with an example configuration.

In FIG. 5B, intramedullary rod 1000b has shaft member 1200b and outer body member 1300b. In this example, each of the shaft member 1200b and the outer body member 1300b in intramedullary rod 1000b has a circular cross-sectional shape. Also, outer body member 1300b is disposed circumferentially and coaxially around shaft member 1200b, similar to the intramedullary rod 1000. In this example, however, the outer surface 1340b of outer body member 1300b defines a series of facets 1375b.

In FIG. 5C, intramedullary rod 1000c has shaft member 1200c and outer body member 1300c. In this example, shaft member 1200c has a circular cross-sectional shape. Outer body member 1300c, however, has a rounded, star-shaped cross-sectional shape such that the outer surface 1340c of outer body member 1300c defines a series of undulations 1375c. Outer body member 1300c is disposed circumferentially and coaxially around shaft member 1200c, similar to the intramedullary rod 1000.

In FIG. 5D, intramedullary rod 1000d has shaft member 1200d and outer body member 1300d. In this example, shaft member 1200d has a circular cross-sectional shape. Outer body member 1300d, however, has an ovoid cross-sectional shape. Outer body member 1300d is disposed circumferentially and coaxially around shaft member 1200d, similar to the intramedullary rod 1000.

In FIG. 5E, intramedullary rod 1000e has shaft member 1200e and outer body member 1300e. In this example, each of shaft member 1200e and outer body member 1300e has an ovoid cross-sectional shape. Outer body member 1300e has a greater thickness on lateral portions that intersect the common minor axis 1375e of the ovoid cross-sectional shapes of the shaft member 1200e and outer body member 1300e, and a lesser thickness on lateral portions that intersect the common major axis 1377e of the ovoid cross-sectional shapes of the shaft member 1200e and outer body member 1300e. Outer body member 1300e is disposed circumferentially and coaxially around shaft member 1200e, similar to the intramedullary rod 1000. Also, intramedullary rod 1000e has a locking screw passageway 1350e that extends through the entire thickness of each of the shaft member 1200e and the outer body member 1300e and along the common major axis 1377e of the ovoid cross-sectional shapes of the shaft member 1200e and outer body member 1300e.

In FIG. 5F, intramedullary rod 1000f has shaft member 1200f and outer body member 1300f. In this example, each of shaft member 1200f and outer body member 1300f has an ovoid cross-sectional shape. Outer body member 1300f has a greater thickness on lateral portions that intersect the common minor axis 1375f of the ovoid cross-sectional shapes of the shaft member 1200f and outer body member 1300f, and a lesser thickness on lateral portions that intersect the common major axis 1377f of the ovoid cross-sectional shapes of the shaft member 1200f and outer body member 1300f. Outer body member 1300f is disposed circumferentially and coaxially around shaft member 1200f, similar to the intramedullary rod 1000. Also, intramedullary rod 1000f has a locking screw passageway 1350f that extends through the entire thickness of each of the shaft member 1200f and the outer body member 1300f and along the common minor axis 1375f of the ovoid cross-sectional shapes of the shaft member 1200f and outer body member 1300f.

It may be desirable to position the shaft member off-axis relative to the outer body member. FIG. 5G illustrates an intramedullary rod 1000g configured in this manner. In this example, each of the shaft member 1200g and the outer body member 1300g in intramedullary rod 1000g has a circular cross-sectional shape. Also, outer body member 1300g is disposed circumferentially and non-coaxially around the shaft member 1200g. Thus, shaft member 1200g has longitudinal axis 1285g and outer body member 1300g has longitudinal axis 1385g that is not aligned with longitudinal axis 1285g of shaft member 1200g. Also, intramedullary rod 1000g has a locking screw passageway 1350g that extends through the entire thickness of each of the shaft member 1200g and the outer body member 1300g. In this example, locking screw passageway 1350g extends along a transverse axis 1287 of shaft member and defines a passageway lumen 1351 that includes both the longitudinal axis 1285g of the shaft member 1200 and the longitudinal axis 1385g of the outer body member 1300.

Figure 3:
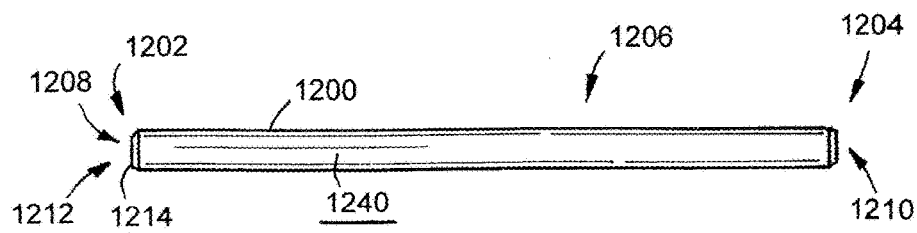
FIG. 3 is an isolated side view of the shaft member of the first example intramedullary rod.

Each of the shaft member and outer body member in an intramedullary rod according to an embodiment can have a configuration that is substantially consistent along the axial length of the intramedullary rod. For example, as best illustrated in FIG. 3, shaft member 1200 of intramedullary rod 1000 has a constant outer diameter along its axial length. Also, as best illustrated in FIG. 1, intramedullary rod 1000 includes outer body member 1300 that has a constant outer diameter along its body 1306, and an outwardly flared portion at its proximal end 1302 and an inwardly tapered portion at its distal end 1304.

Figure 6A:
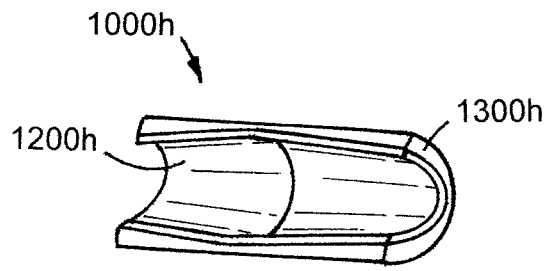
FIG. 6A is a partial perspective view of another alternative intramedullary rod.
Figure 6B:
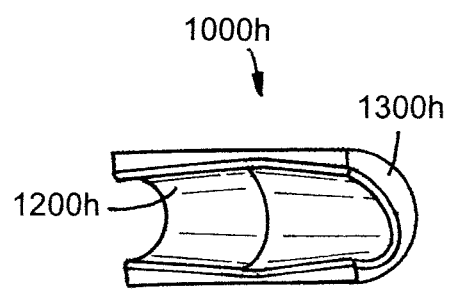
FIG. 6B is a partial perspective view of another alternative intramedullary rod.

Each of FIGS. 6A through 6B illustrates an alternative intramedullary rod 1000h having a shaft member 1200h and outer body member 1300h with an example configuration. In this example, as best illustrated in FIG. 6A, the outer body member 1300h has a thickness that varies along the axial length of the intramedullary rod 1300h. Also in this example, as best illustrated in FIG. 6B, the shaft member 1200h has a configuration that varies along the axial length of the intramedullary rod 1300h. In the figure, the shaft member 1200h has a substantially circular cross-sectional shape at the portion on the left side of the figure and a substantially ovoid cross-sectional shape at the portion on the right side of the figure.

Figure 7A:
FIG. 7A is a side view of another alternative intramedullary rod.
Figure 7B:
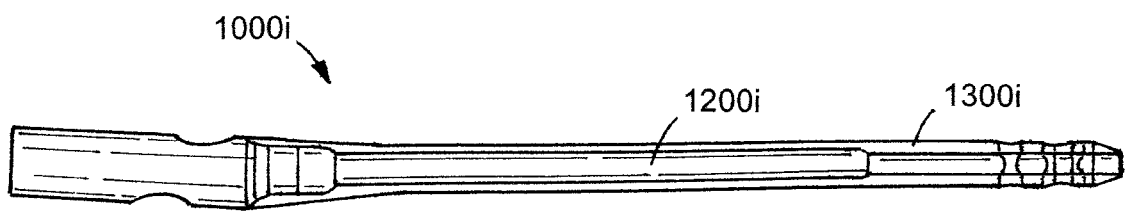
FIG. 7B is a side view of another alternative intramedullary rod.
Figure 7C:
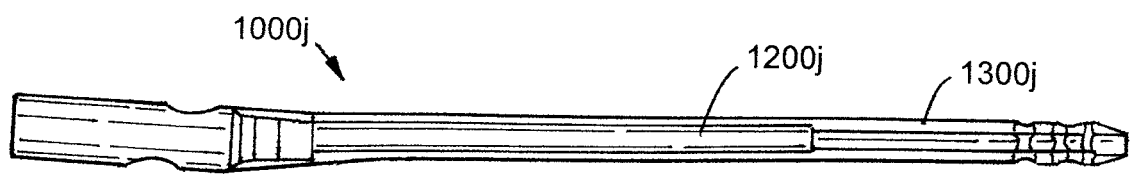
FIG. 7C is a side view of another alternative intramedullary rod.

Each of the shaft member and outer body member in an intramedullary rod according to an embodiment can have any suitable axial length. Furthermore, the shaft member and outer body member in an intramedullary rod according to an embodiment can have any suitable relative lengths. A skilled artisan will be able to select suitable axial lengths, and relative axial lengths, for the shaft member and outer body member in an intramedullary rod according to a particular embodiment based on various considerations, including the nature of the bone with which the intramedullary rod is intended to be used, the nature of the materials used for the shaft member and the outer body member, and other considerations. The axial lengths, and relative axial lengths, illustrated herein provide examples of axial lengths and relative axial lengths considered suitable for intramedullary rods. For example, FIG. 7A illustrates the first example intramedullary rod 1000. In this example, the shaft member 1200 has an axial length that is less than the axial length of the outer body member 1300. Indeed, the shaft member 1200 has an axial length that is greater than about 50% of the axial length of the outer body member 1300 but less than about 80% of the axial length of the outer body member 1300. FIG. 7B illustrates an alternative intramedullary rod 1000i having a shaft member 1200i and outer body member 1300i with an example configuration. In this example, the shaft member 1200i has an axial length that is greater than about 50% of the axial length of the outer body member 1300i but less than about 75% of the axial length of the outer body member 1300i. FIG. 7C illustrates an alternative intramedullary rod 1000j having a shaft member 1200j and outer body member 1300j with an example configuration. In this example, the shaft member 1200j has an axial length that is greater than about 50% of the axial length of the outer body member 1300j but less than about 70% of the axial length of the outer body member 1300j.

Figure 8A:
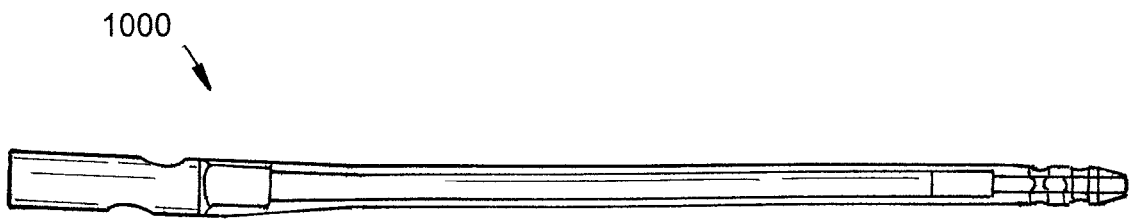
FIG. 8A is a side view of another alternative intramedullary rod.
Figure 8B:
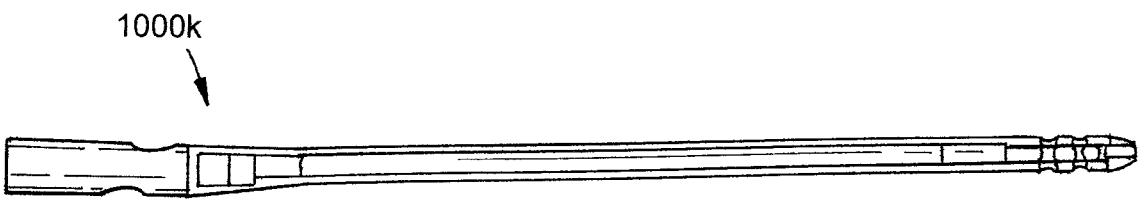
FIG. 8B is a side view of another alternative intramedullary rod.
Figure 8C:
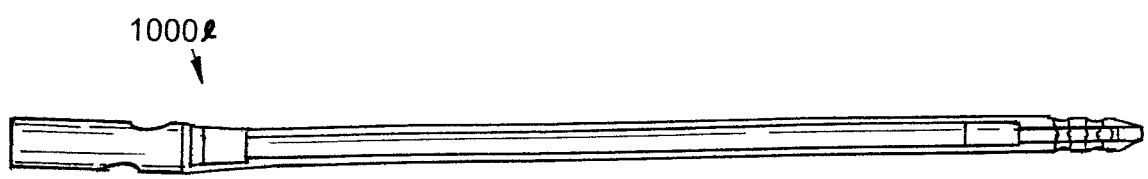
FIG. 8C is a side view of another alternative intramedullary rod.
Figure 8D:
FIG. 8D is a side view of another alternative intramedullary rod.

Each of the shaft member and outer body member in an intramedullary rod according to an embodiment can have any outer diameter. Furthermore, the shaft member and outer body member in an intramedullary rod according to an embodiment can have any suitable relative outer diameters. A skilled artisan will be able to select suitable outer diameters, and relative outer diameters, for the shaft member and outer body member in an intramedullary rod according to a particular embodiment based on various considerations, including the nature of the bone with which the intramedullary rod is intended to be used, the nature of the materials used for the shaft member and the outer body member, and other considerations. The outer diameters, and relative outer diameters, illustrated herein provide examples of outer diameters and relative outer diameters considered suitable for intramedullary rods. For example, FIG. 8A illustrates the first example intramedullary rod 1000. Each of FIGS. 8B, 8C, and 8D illustrates an alternative intramedullary rod.

Figure 9:
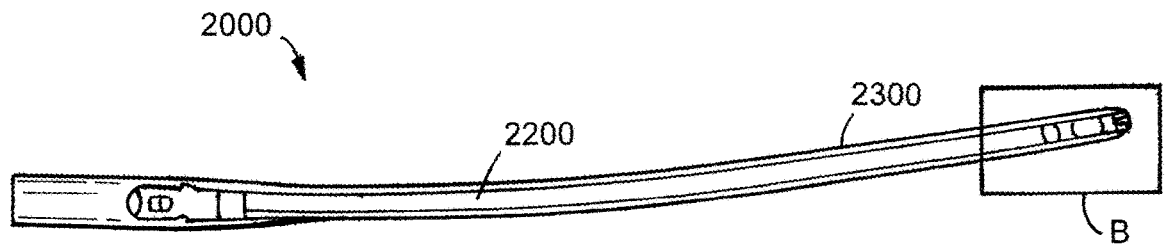
FIG. 9 is a side view of a second example intramedullary rod.
Figure 9A:
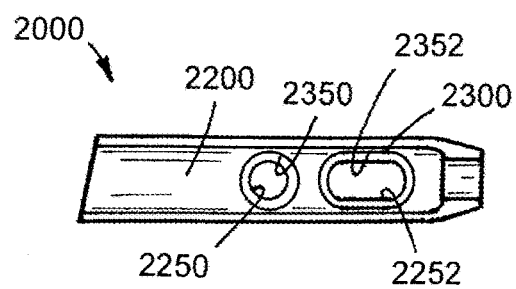
FIG. 9A is a magnified view of Area B of FIG. 9.

FIGS. 9 and 9A illustrate another example intramedullary rod 2000. In this example, the shaft member 2200 extends axially to a distal end 2204 that is disposed adjacent, but inwardly of, the distal end 2304 of the outer body member 2300. Also, as best illustrated in FIG. 9A, the shaft member 2200 defines first 2250 and second 2252 locking screw passageways that align with the first 2350 and second 2352 locking screw passageways defined by the outer body member 2300.

Figures 10A, 10B, 10C:
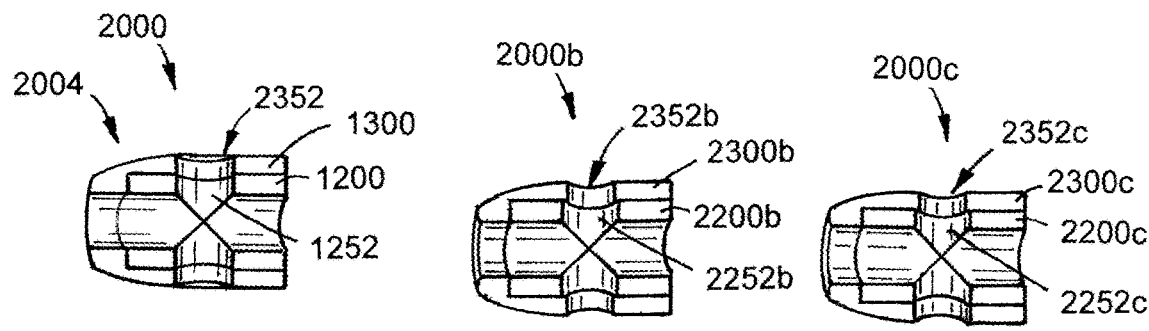
FIG. 10A is a partial magnified cross-sectional view of the distal end of the second example intramedullary rod.
FIG. 10B is a partial magnified cross-sectional view of the distal end of an alternative intramedullary rod.
FIG. 10C is a partial magnified cross-sectional view of the distal end of another alternative intramedullary rod.
Figure 11:
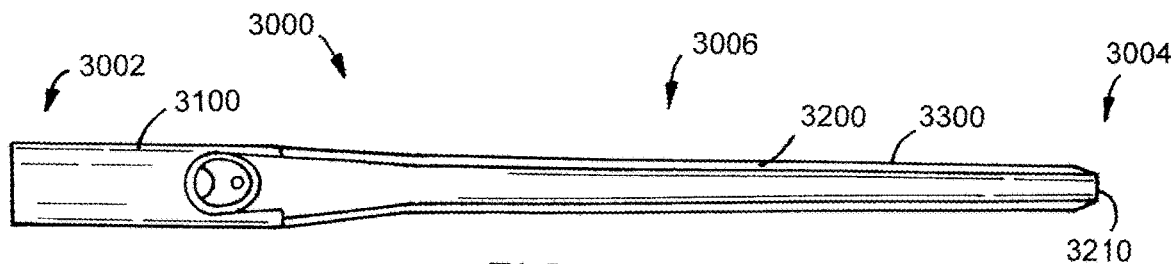
FIG. 11 is a top view of a third example intramedullary rod.

In embodiments in which the shaft member defines one or more locking screw passageways that are aligned with locking screw passageways of the outer body member, various structural arrangements are possible and contemplated. For example, FIG. 10A illustrates the distal end 2004 of the intramedullary rod 2000 illustrated in FIGS. 9 and 9A. In this example, second locking screw passageway 2252 defined by the shaft member 2200 has the same inner diameter of the second locking screw passageway 2352 defined by the outer body member 2300. As a result, both the openings defined in the walls of the shaft member 2200n have the same diameter as those of the openings defined by the walls of the outer body member 2300. FIG. 10B illustrates another example intramedullary rod 2000b. In this example, second locking screw passageway 2252b defined by the shaft member 2200b has a larger inner diameter than the inner diameter of the second locking screw passageway 2352b defined by the outer body member 2300b. As a result, both of the openings defined in the walls of the shaft member 2200b have larger diameters than those of the openings defined by the walls of the outer body member 2300b. FIG. 10C illustrates another example intramedullary rod 2000c. In this example, second locking screw passageway 2252c defined by the shaft member 2200c has a larger inner diameter than the inner diameter of the second locking screw passageway 2352c defined by the outer body member 2300c on one side of the intramedullary rod 2000c; on the opposite side, second locking screw passageway 2252c defined by the shaft member 2200c has the same inner diameter than the inner diameter of the second locking screw passageway 2352c defined by the outer body member 2300c. As a result, one of the openings defined in the wall of the shaft member 2200c has a larger diameter than the adjacent opening defined by the wall of the outer body member 2300c while the other of the openings defined in the wall of the shaft member 2200c has the same diameter as the adjacent opening defined by the wall of the outer body member 2300c.

FIGS. 11, 12, 13 and 14 illustrate a third example intramedullary rod 3000 or a portion of the first example intramedullary rod 3000. The intramedullary rod 3000 is similar to the intramedullary rod 1000 described above, except as detailed below. Thus, intramedullary rod 3000 has a proximal end 3002, a distal end 3004, and a body 3006 extending between the proximal end 3002 and the distal end 3004. The intramedullary rod 3000 includes a head member 3100, a shaft member 3200 partially disposed within the head member 3100, and an outer body member 3300 disposed circumferentially around the shaft member 3200 and a portion of the head member 3100. A device lumen 3024 extends through the entire axial length of the intramedullary rod 3000 from a proximal opening 3102 of the head member 3100 to a distal opening 3210 of the shaft member 3200, placing the entire device lumen 3024 in communication with the environment external to the intramedullary rod 3000. As such, the intramedullary rod 3000 is a cannulated rod, allowing it to be passed over a separate member, such as a wire, to facilitate placement and/or positioning during implantation.

Figure 12:
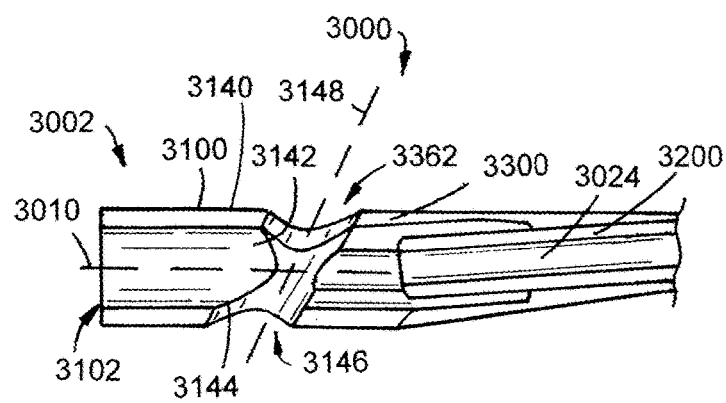
FIG. 12 is a sectional view, partially broken away, of the third example intramedullary rod.
Figure 13:
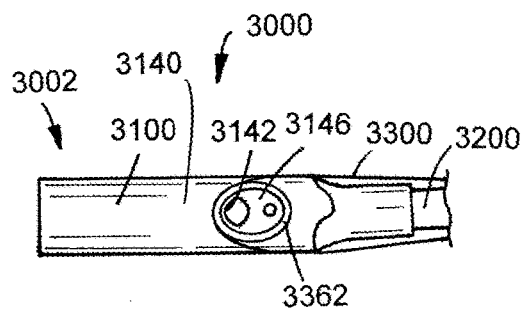
FIG. 13 is a top view, partially broken away, of the third example intramedullary rod.
Figure 14:
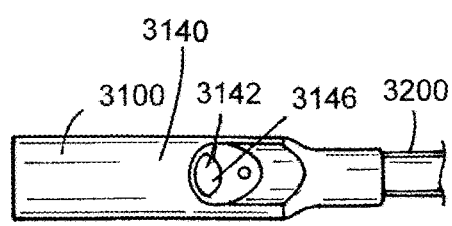
FIG. 14 is a top view, partially broken away, of the head-shaft assembly of the third example intramedullary rod.

In this example, head member 3100 defines has an outer surface 3140 that defines a first opening 3142 on a first axial side of the body 3106 and a second opening 3144 positioned a second, opposite axial side of the body 3106. A passageway 3146 extends from the first opening 3142 to the second opening 3144. As best illustrated in FIG. 12, the passageway 3146 extends along an axis 3148 that is disposed at a transverse angle to the first longitudinal axis 3010 of the intramedullary rod 3000. The passageway 3146 is sized and configured to receive a lag screw used for securing the intramedullary rod 3000 to a bone.

As best illustrated in FIG. 12, outer body member 3300 extends axially beyond the proximal end 3202 of shaft member 3200. Furthermore, outer body member 3300 defines an opening 3362 that provides access to passageway 3146 defined by head member 3100. As best illustrated in FIG. 12, opening 3362 has a slightly smaller inner diameter than the inner diameter of first opening 3142 defined by head member 3100. This structural arrangement is considered advantageous at least because it provides a portion of the outer body member 3300 as sacrificial material at the openings 3362, 3142 to the passageway 3146 that provides protection against interaction between a lag screw and the head member 3100, which may prevent damage and/or notching of the head member that can result when a lag screw or reaming tool is used to place a lag screw in a passageway defined by a head member of an intramedullary rod. In embodiments that include this structural arrangement, the material of the outer body member 3300 interacts with a lag screw or reamer, and can incur the damage and/or notching that can occur as a result, protecting the head member 3100 from such damage and/or notching. This, in turn, provides a more stable connection between the intramedullary rod 3000, the lag screw, and any bones to which the intramedullary rod 3000 and lag screw are secured.

Figure 18:
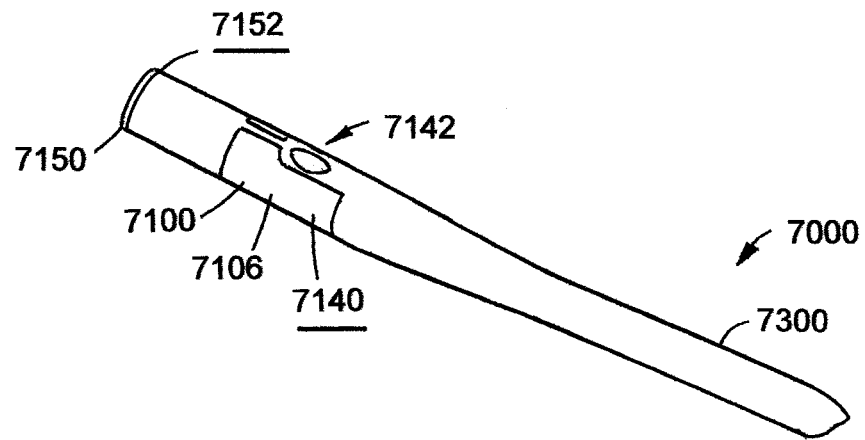
FIG. 18 is a perspective view of another example intramedullary rod.
Figure 19:
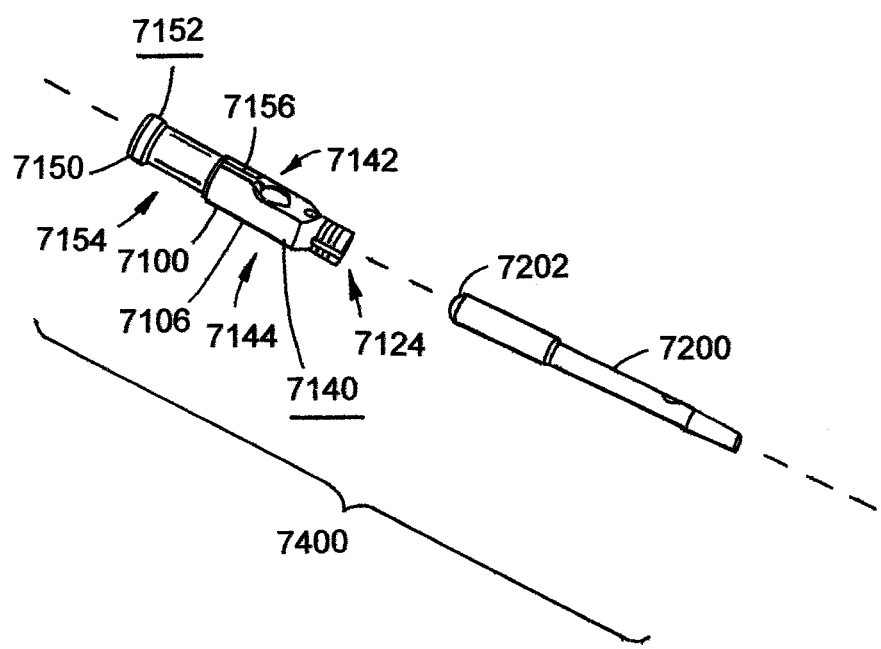
FIG. 19 is an exploded view of a head-shaft assembly of the example intramedullary rod illustrated in FIG. 18.

FIG. 18 illustrates another example intramedullary rod 7000; FIG. 19 illustrates a head-shaft assembly 7400 formed when the proximal end 7202 of the shaft member 7200 is disposed within the cavity 7124 of the head member 7100. In this example, the head member 7100 defines a proximal flange 7150 that extends radially outward to define a surface 7152 that, in the assembled intramedullary rod 7000, is in contact with the outer body member 7300. Inclusion of the proximal flange 7150 is considered advantageous at least because it provides a surface 7152 against which the material used to form the outer body member 7300 during manufacturing can bond, attach, seal, or otherwise interface with. Also in this example, the body 7106 of the head member 7100 has an outer surface 7140 that defines a first opening 7142 on a first axial side of the body 7106 and a second opening 7144 positioned a second, opposite axial side of the body 7106. As best illustrated in FIG. 18, the outer body member 7300 extends completely around the first opening 7142 on the first axial side of the body 7106. While not illustrated in the Figure, it is noted that the outer body member 7300 can optionally also extend completely around the second opening 7144 on the second axial side of the body 7106. It is noted, though, that the outer body member 7300 can also partially extend around the second opening 7144. Also alternatively, the outer body member 7300 can be formed such that it does not extend, either partially or completely, around the second opening 7144.

Also in this example, the outer surface 7140 of the head member 7100 defines a circumferential channel 7154 adjacent the proximal flange 7150. The circumferential channel 7154 has an outer diameter that is less than the outer diameter of the body 7106 of the head member 7100. Also, the body 7106 of the head member 7100 defines a longitudinal groove 7156 that extends from the first opening 7142 on the first axial side of the body 7106 to the circumferential channel 7154. While not visible in the Figures, it is noted that the body 7106 of the head member 7100 can define a second longitudinal groove extending from the second opening 7144 to the circumferential channel 7154, such as a longitudinal groove that is disposed on the body 7106 of the head member 7100 diametrically opposite of longitudinal groove 7156. As best illustrated in FIG. 18, inclusion of the circumferential channel 7154 and longitudinal groove is considered advantageous at least because both of these features provide structural definition within which portions of the outer body member 7300 can be disposed, which can contribute structural benefits to the intramedullary rod 7000.

Figure 20:
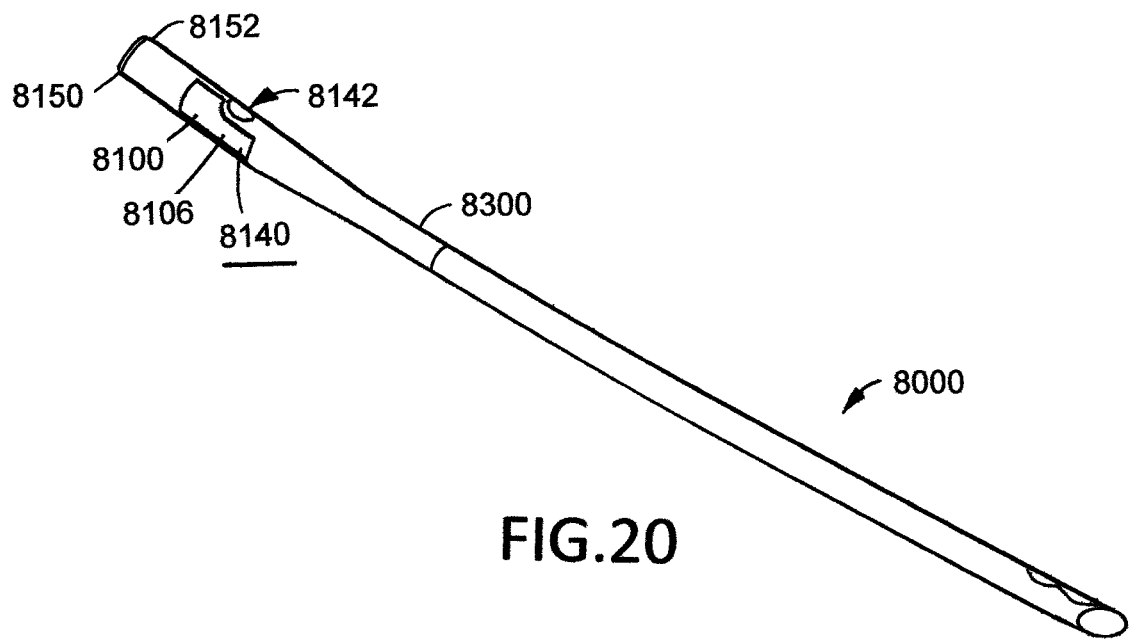
FIG. 20 is a perspective view of another example intramedullary rod.
Figure 21:
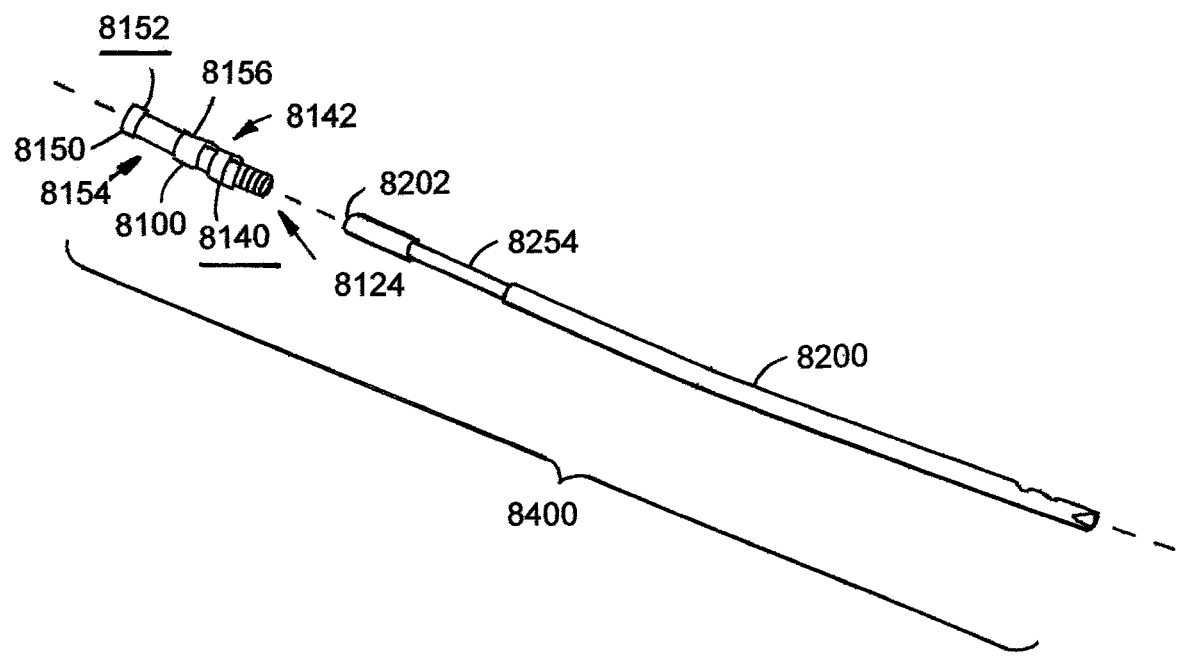
FIG. 21 is an exploded view of a head-shaft assembly of the example intramedullary rod illustrated in FIG. 20.

FIG. 20 illustrates another example intramedullary rod 8000; FIG. 21 illustrates a head-shaft assembly 8400 formed when the proximal end 8202 of the shaft member 8200 is disposed within the cavity 8124 of the head member 8100. The example intramedullary rod 8000 is similar to the example intramedullary rod 7000 illustrated in FIG. 18 and described above, except as detailed below. Thus, in this example, the head member 8100 defines a proximal flange 8150 that extends radially outward to define a surface 8152 that, in the assembled intramedullary rod 8000, is in contact with the outer body member 8300. The body 8106 of the head member 8100 has an outer surface 8140 that defines a first opening 8142 on a first axial side of the body 8106 and a second opening 8144 positioned a second, opposite axial side of the body 8106. As best illustrated in FIG. 20, the outer body member 8300 extends completely around the first opening 8142 on the first axial side of the body 8106. The outer surface 8140 of the head member 8100 defines a circumferential channel 8154 adjacent the proximal flange 8150. The circumferential channel 8154 has an outer diameter that is less than the outer diameter of the body 8106 of the head member 8100. Also, the body 8106 of the head member 8100 defines a longitudinal groove 8156 that extends from the first opening 8142 on the first axial side of the body 8106 to the circumferential channel 8154.

In this embodiment, as best illustrated in FIG. 21, the shaft member 8200 defines a circumferential channel 8254 near the proximal end 8202 of the shaft member 8200. The circumferential channel 8254 has an outer diameter that is less than the outer diameter of the portion of the body 8206 of the shaft member 8200 that extends between the circumferential channel 8254 and the distal end 8204 of the shaft member 8200. In the illustrated example intramedullary rod 8000, a portion of the body 8206 of the shaft member 8200 having a greater outer diameter than that of the circumferential channel 8254 is disposed between the circumferential channel 8254 and the proximal end 8202 of the shaft member 8200. It is noted, though, that as an alternative to the circumferential channel 8254, a circumferential recess that extends to the proximal end 8202 of the shaft member 8200 can be included.

Also in this embodiment, the outer body member 8300 extends along the shaft member 8200 only to the distal end of the circumferential channel 8254, as best illustrated in FIG. 20. This structural arrangement is considered advantageous at least because the circumferential channel 8254 on the shaft member 8200 and the circumferential channel 8154 on the head member 8100 cooperatively define axial limiting surfaces for the outer body member 8300, which can be beneficial in the manufacturing of intramedullary rods, and particularly for relatively long intramedullary rods.

In all embodiments, the shaft member can be made of any material suitable for use in medical devices intended for orthopedic use, including use as a long-term implant. Examples of suitable materials include metals, metal alloys, and polymeric materials. Examples of suitable metals include, but are not limited to, Titanium, Magnesium, and other metals. Examples of suitable metal alloys include, but are not limited to, Ti6Al4V, 316 LVM, 1.4441Ti-13Nb-13Zr, Ti-12Mo-6Zr-2Fe, Ti-15Mo-5Zr-3Al, Ti-15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys. Examples of suitable polymeric materials include, but are not limited to, polyaryletherketone (PAEK), polyether ether ketone (PEEK), PEEK (90G, 450G, I2, I4), Polyamid, PA66, carbon fiber reinforced polyaryletherketone (CFR PAEK), polyether ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, I2 CF20, I2 CF30, I4 CF30, I4 CF20), Polyamid CFR, and PA66 CFR.

In all embodiments, the outer body member can be made of any material suitable for use in medical devices intended for orthopedic use, including use as a long-term implant. Examples of suitable types of materials include, but are not limited to, polymeric materials, composite materials, and other materials. Examples of suitable polymeric materials include, but are not limited to, PAEK, CFR PAEK, PEKK, CFR PEKK, PEEK, CFR-PEEK, PEEK (90G, 450G, I2, I4), Polyamid, and PA66.

Examples of suitable composite materials include, but are not limited to, polyether ether ketone (PEEK)-Carbon composite materials. The use of PEEK-Carbon composite materials is considered particularly advantageous as they provide desirable manufacturing properties, including the ability to form the outer body member in an intramedullary rod according to a particular embodiment around the shaft member using injection molding techniques and processes. In these embodiments, any suitable PEEK-Carbon composite material can be used, and a skilled artisan will be able to select a suitable PEEK-Carbon material for an outer body member in an intramedullary rod according to a particular embodiment based on various considerations, including the configuration of the shaft member, any desired physical properties, such as flexibility and bendability of the intramedullary rod, and other considerations. The inventors have determined that use of a PEEK-Carbon composite material having between about 10% and about 40% carbon fibers by weight provides an outer body member and intramedullary rod having desirable physical properties and manufacturability.

Examples of suitable blended materials include, but are not limited to, PEEK-Carbon materials, CFR PAEK, CFR PEKK, CFR PEEK (90G CA30, 90G CA20, 450G CA30, 450G CA20, I2 CF20, I2 CF30, I4 CF30, I4 CF20), Polyamid CFR, PA66 CFR.

It is noted that the materials used in a component of an intramedullary rod according to a particular embodiment can include additives, coatings, fillers, and/or other elements if desired. For example, antibiotics, bioactive glass, silver, copper, or another material that can reduce bacterial colonization of the intramedullary rod following implantation can be included in the material of the shaft member, the outer body member, or both. Furthermore, one or more components of an intramedullary rod according to an embodiment can be treated in a manner that facilitates making of the intramedullary rod, provides structural benefit to the intramedullary rod, or that provides other advantages. For example, in embodiments in which the shaft member comprises a metal, the inventors have determined that anodizing the shaft member in an intramedullary rod according to an embodiment prior to overmolding the shaft member with a suitable material to form the outer body member can be advantageous at least because anodization provides additional surface area on the shaft member to which the material of the outer body member can attach or bond during the overmolding process. Accordingly, an intramedullary rod according to any example described herein, or any other embodiment, can include a metal shaft member that comprises an anodized shaft member. In these embodiments, conventional anodization processes can be used to prepare the metal shaft member prior to overmolding the outer body member to form the intramedullary rod.

The inventors have determined that an intramedullary rod having a shaft member formed of a Titanium alloy, such as Ti6Al4V, and an outer body member formed of CFR PEEK provides desirable characteristics and a favorable balance between manufacturability and strength considerations.

Figure 15:
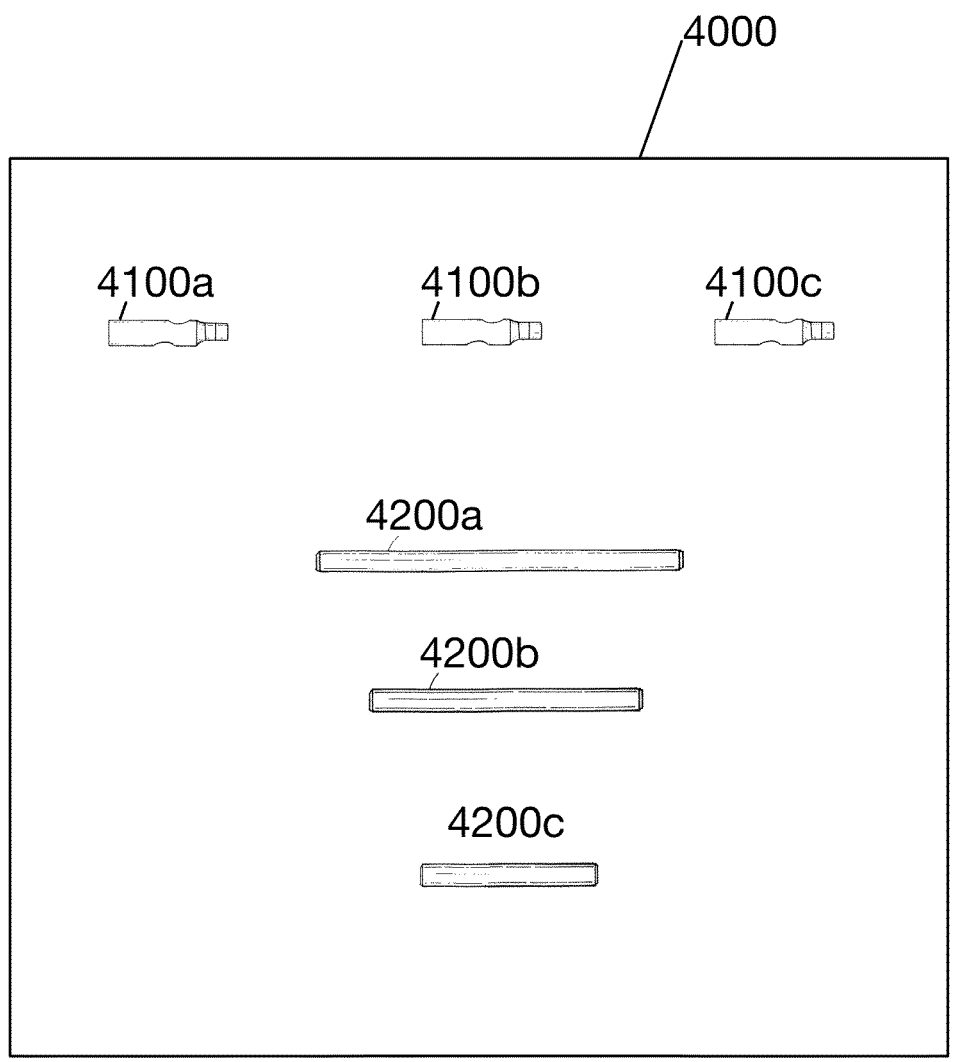
FIG. 15 is a schematic representation of an example medical device system.

FIG. 15 is a schematic representation of a medical device system 4000. The medical device system 4000 comprises a plurality of a head members 4100a, 4100b, 4100c, and a plurality of shaft members 4200a, 4200b, and 4200c. The medical device system 4000 provides a modular system that enables efficient manufacturing of intramedullary rods. As such, the medical device system 4000 can be used in the manufacturing of medical devices, such as in one or more of the methods described herein.

In the example medical device system 4000, the head members 4100a, 4100b, 4100c are identical to each other. Accordingly, each of the plurality of head members 4100a, 4100b, 4100c has a proximal end 4102a, 4102b, 4102c, a distal end 4104a, 4104b, 4104c, and a body 4106a, 4106b, 4106c extending between the respective proximal end 4102a, 4102b, 4102c and the respective distal end 4104a, 4104b, 4104c. The proximal end 4102a, 4102b, 4102c of each head member 4100a, 4100b, 4100c defines a proximal opening 4108a, 4108b, 4108c. The distal end 4104a, 4104b, 4104c of each head member 4100a, 4100b, 4100c defines a distal opening 4110a, 4110b, 4110c. Also, each head member 4100a, 4100b, 4100c defines a head member lumen 4112a, 4112b, 4112c extending between the respective proximal opening 4108a, 4108b, 4108c and the respective distal opening 4110a, 4110b, 4110c.

In the illustrated medical device system 4000, each of the shaft members 4200a, 4200b, 4200c has a different axial length than the other shaft members 4200a, 4200b, 4200c while having the same diameter as the other shaft members 4200a, 4200b, 4200c. Thus, the first shaft member 4200a has an axial length that is greater than the axial length of the second shaft member 4200b and the axial length of the third shaft member 4200c. The second shaft member 4200b has an axial length that is less than the axial length of the first shaft member 4200a and greater than the axial length of the third shaft member 4200c. The third shaft member 4200c has an axial length that is less than the axial length of the first shaft member 4200a and the axial length of the second shaft member 4200b. In some embodiments, first and second sets of shaft members are included in the medical device system. In these embodiments, each of the shaft members in the first set of shaft members share a common dimension that defines the set and that distinguishes the set from the second set of shaft members. For example, the common dimension can be an axial length of the shaft members. In these embodiments, each of the shaft members in the first set of shaft members is identical to all other shaft members in the first set of shaft members. Similarly, each of the shaft members in the second set of shaft members is identical to all other shaft members in the second set of shaft members. In these embodiments, any number of additional sets of shaft members can be included in the medical device system. For example, a third set of shaft members can be included. In this example, each of the shaft members in the third set of shaft members is identical to all other shaft members in the third set of shaft members but is different from all shaft members in the first set of shaft members and the second set of shaft members on at least one dimension, such as the axial length of the shaft members. In these examples, any suitable number of sets of shaft members can be included.

Any suitable number of head members can be included in a medical device system according to a particular embodiment. Examples of suitable numbers of head members for inclusion in a medical device system according to a particular embodiment include, but are not limited to, one, one or more, two, two or more, a plurality, three, four, five, six, seven, eight, nine, ten, ten or more, eleven, twelve, a dozen, dozens, one hundred, one thousand, and multiples thereof.

Any suitable number of shaft members can be included in a medical device system according to a particular embodiment. Examples of suitable numbers of shaft members for inclusion in a medical device system according to a particular embodiment include, but are not limited to, one, one or more, two, two or more, a plurality, three, four, five, six, seven, eight, nine, ten, ten or more, eleven, twelve, a dozen, dozens, one hundred, one thousand, and multiples thereof.

Also, in embodiments in which the medical device system includes a first set of shaft members and a second set of shaft members, the first set of shaft members can include any suitable number of shaft members and the second set of shaft members can include any suitable number of shaft members. Examples of suitable numbers for each of the first set of shaft members and the second set of shaft members include one, one or more, two, two or more, plurality, three, four, five, six, seven, eight, nine, ten, ten or more, eleven, twelve, a dozen, dozens, one hundred, one thousand, and multiples thereof. Furthermore, in these embodiments, the first and second sets of shaft members can have the same or different numbers of shaft members. For example, a medical device system according to an embodiment can include a first set of shaft members and a second set of shaft members having the same number of shaft members as the first set of shaft members. Also as an example, a medical device system according to an embodiment can include a first set of shaft members and a second set of shaft members having fewer shaft members than the first set of shaft members. Also as an example, a medical device system according to an embodiment can include a first set of shaft members and a second set of shaft members having more shaft members than the first set of shaft members.

The medical device system 4000 enables a user to select a head member 4100a, 4100b, 4100c without regard for dimension or other considerations since all head members 4100a, 4100b, 4100c are identical. Then, the user can select a shaft member 4200a, 4200b, 4200c with regard to a desired dimension. Using the selected components, the user can proceed to manufacture a medical device, such as an intramedullary rod, such as performing one or more of the methods described herein.

Figure 16:
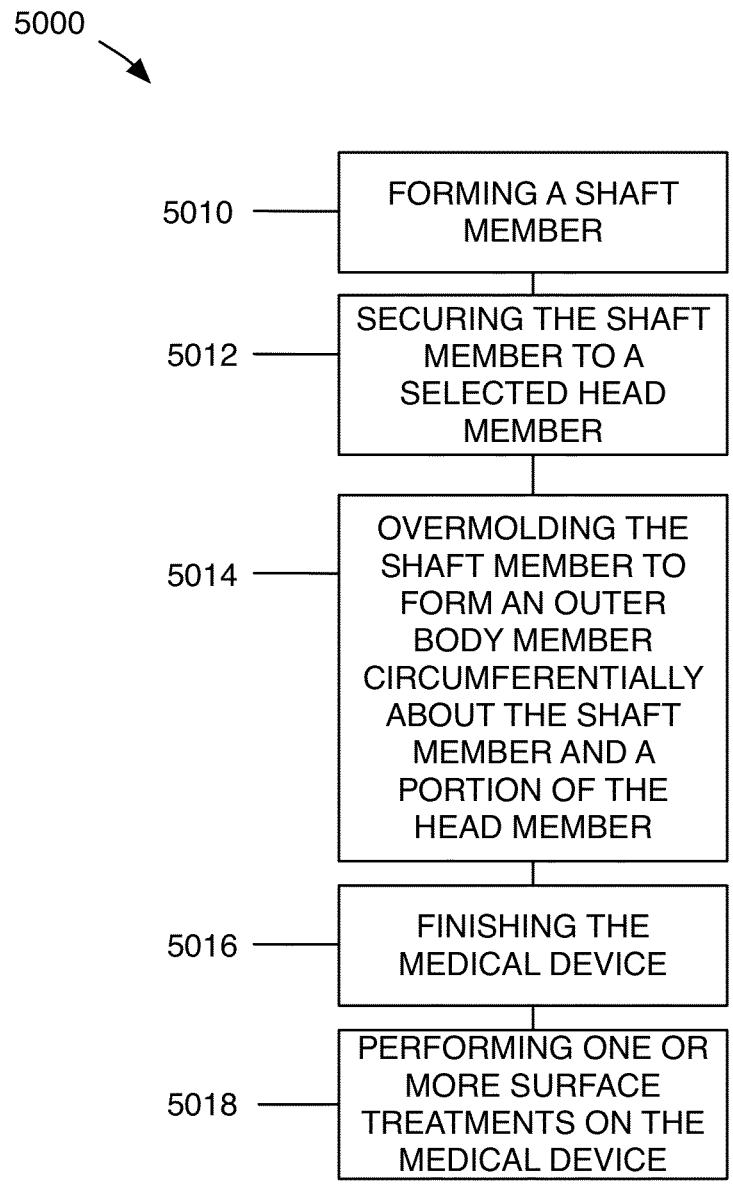
FIG. 16 is a flowchart representation of an example method of manufacturing an intramedullary rod.

FIG. 16 is a schematic representation of a method 5000 of manufacturing an intramedullary rod. An initial step 5010 comprises forming a shaft member from a suitable precursor, such as a solid rod or cannula. This step can be performed to form a suitable shaft member, such as any of the shaft members described and/or illustrated herein. A next step 5012 comprises securing the shaft member to a selected head member. The selected head member can be any suitable head member, such as any of the head members described and/or illustrated herein. A next step 5014 comprises overmolding the shaft member with a suitable material to form the outer body member circumferentially about the shaft member and a portion of the head member in accordance with an embodiment of the invention, including any of the examples described and/or illustrated herein. At this point, a medical device, such as an intramedullary rod, is available. It may be desirable, however, to include additional steps, such as step 5016, which comprises finishing the medical device using suitable techniques or processes. Another additional optional step 5018 comprises performing one or more surface treatments on the medical device, such as roughening, coating, and the like. An optional step, not illustrated in FIG. 16, includes anodizing the shaft member prior to the step 5014 of overmolding the shaft member with a suitable material to form the outer body member circumferentially about the shaft member and a portion of the head member. Inclusion of this step can be advantageous in methods of making an intramedullary rod in which it is desirable to increase the surface area on the shaft member to which the material of the outer body member can attach or bond during the step 5014 of overmolding the shaft member with a suitable material to form the outer body member.

Figure 17:
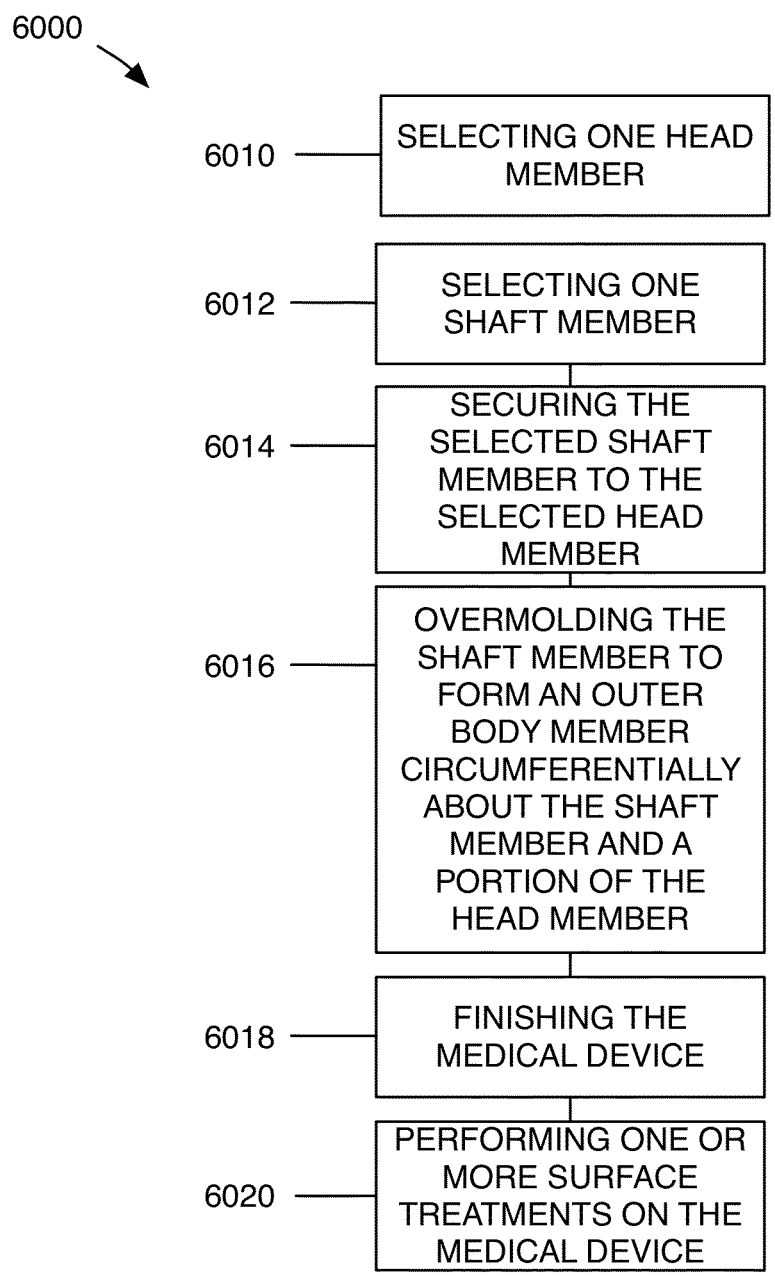
FIG. 17 is a flowchart representation of another example method of manufacturing an intramedullary rod.

FIG. 17 is a schematic representation of a method 6000 of manufacturing an intramedullary rod. An initial step 6010 comprises selecting one head member from a medical device system comprising a two or more identical head members and two or more shaft members having different axial lengths. Another step 6012 comprises selecting one shaft member from the two or more shaft members of the medical device system. Another step 6014 comprises securing the selected shaft member to the selected head member. Another step 6016 comprises overmolding the shaft member with a suitable material to form an outer body member circumferentially about the shaft member and a portion of the head member in accordance with an embodiment of the invention, including any of the examples described and/or illustrated herein. At this point, a medical device, such as an intramedullary rod, is available. It may be desirable, however, to include additional steps, such as step 6018, which comprises finishing the medical device using suitable techniques or processes. Another additional optional step 6020 comprises performing one or more surface treatments on the medical device, such as roughening, coating, and the like. An optional step, not illustrated in FIG. 17, includes anodizing the shaft member prior to the step 6016 of overmolding the shaft member with a suitable material to form the outer body member circumferentially about the shaft member and a portion of the head member. Inclusion of this step can be advantageous in methods of making an intramedullary rod in which it is desirable to increase the surface area on the shaft member to which the material of the outer body member can attach or bond during the step 6016 of overmolding the shaft member with a suitable material to form the outer body member.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention are not intended to limit the scope of the invention or its protection, which is to be given the full breadth of the appended claims and any and all equivalents thereof.

We claim:

1. An intramedullary rod, comprising:
   a head member having a proximal head member end, a distal head member end, a head member distal extension defining a head member cavity, a head member lumen extending between the proximal head member end and the distal head member end, and a head member outer surface, a first opening on a first axial side of the head member, a second opening on a second axial side of the head member, and a passageway extending between the first opening and the second opening;

a shaft member having a shaft member proximal end disposed within the head member cavity, the shaft member having a proximal shaft member opening, a distal shaft member opening, and defining a shaft member lumen extending between the proximal shaft member opening and the distal shaft member opening, the shaft member lumen positioned in line with the head member lumen; and an outer body member disposed circumferentially around the shaft member and a portion of the head member, the outer body member defining an outer body member opening disposed over the first opening of the head member;

wherein the head member defines a proximal flange and a circumferential channel disposed adjacent the proximal flange.

2. The intramedullary rod of claim 1, wherein the head member defines a longitudinal groove extending from the first opening to the circumferential channel.

3. The intramedullary rod of claim 2, wherein the outer body member includes a portion disposed in the longitudinal groove.

4. The intramedullary rod of claim 3, wherein the outer body member includes a portion disposed in the circumferential channel.

5. The intramedullary rod of claim 4, wherein the shaft member defines a second circumferential channel having a proximal end and a distal end.

6. The intramedullary rod of claim 5, wherein the outer body member extends along the shaft member to the distal end of the second circumferential channel.

7. The intramedullary rod of claim 1, wherein the outer body member opening has a first inner diameter and the first opening of the head member has a second inner diameter; and wherein the first inner diameter is different than the second inner diameter.

8. The intramedullary rod of claim 7, wherein the first inner diameter is less than the second inner diameter.

9. The intramedullary rod of claim 1, wherein the outer body member opening extends completely around the first opening of the head member.

10. The intramedullary rod of claim 1, wherein the outer body member has an outer body member distal end that defines a first outer body member locking screw passageway that extends through the outer body member.

11. The intramedullary rod of claim 10, wherein the shaft member has a shaft member distal end that defines a first shaft member locking screw passageway that aligns with the first outer body member locking screw passageway.

12. The intramedullary rod of claim 11, wherein the first shaft member locking screw passageway has a first inner diameter and the first outer body member locking screw passageway has a second inner diameter; and wherein the first inner diameter is the same as the second inner diameter.

13. The intramedullary rod of claim 11, wherein the first shaft member locking screw passageway has a first inner diameter and the first outer body member locking screw passageway has a second inner diameter; and wherein the first inner diameter is larger than the second inner diameter.

14. The intramedullary rod of claim 11, wherein the outer body member distal end defines a second outer body member locking screw passageway that extends through the outer body member; and wherein the shaft member distal end defines a second shaft member locking screw passageway that aligns with the second outer body member locking screw passageway.

15. The intramedullary rod of claim 1, wherein the shaft member is anodized.

16. The intramedullary rod of claim 15, wherein the shaft member comprises a titanium alloy.

17. The intramedullary rod of claim 16, wherein the outer body member comprises PEEK.

18. The intramedullary rod of claim 16, wherein the outer body member comprises a carbon fiber reinforced polymer.

19. The intramedullary rod of claim 18, wherein the outer body member comprises CFR PEEK.

20. The intramedullary rod of claim 1, wherein the outer body member extends axially beyond the shaft member proximal end.

* * * * *